United States Patent
Baker et al.

(10) Patent No.: US 9,943,237 B2
(45) Date of Patent: Apr. 17, 2018

(54) ANALYSIS OF DIRECT AND INDIRECT HEARTBEAT DATA VARIATIONS

(71) Applicant: Welch Allyn, Inc., Skaneateles Falls, NY (US)

(72) Inventors: Steven D. Baker, Beaverton, OR (US); Eric Glen Petersen, Beaverton, OR (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 522 days.

(21) Appl. No.: 14/559,405

(22) Filed: Dec. 3, 2014

(65) Prior Publication Data

US 2015/0201859 A1    Jul. 23, 2015

Related U.S. Application Data

(60) Provisional application No. 61/911,604, filed on Dec. 4, 2013.

(51) Int. Cl.
| | | |
|---|---|---|
| A61B 5/024 | (2006.01) | |
| A61B 5/0456 | (2006.01) | |
| A61B 5/021 | (2006.01) | |
| A61B 5/02 | (2006.01) | |
| A61B 5/00 | (2006.01) | |

(52) U.S. Cl.
CPC ........ *A61B 5/02405* (2013.01); *A61B 5/0456* (2013.01); *A61B 5/0006* (2013.01); *A61B 5/02007* (2013.01); *A61B 5/02108* (2013.01)

(58) Field of Classification Search
CPC .............. A61B 5/0006; A61B 5/02007; A61B 5/02108; A61B 5/02405; A61B 5/0456
USPC ........ 600/481, 483, 485, 500–503, 509, 513
See application file for complete search history.

(56) References Cited

U.S. PATENT DOCUMENTS

| | | | | |
|---|---|---|---|---|
| 4,573,478 A | * | 3/1986 | Arnold ................. | A61B 5/0245 600/483 |
| 5,687,738 A | | 11/1997 | Shapiro et al. | |
| 5,743,856 A | * | 4/1998 | Oka .................... | A61B 5/02116 600/485 |

(Continued)

FOREIGN PATENT DOCUMENTS

| | | |
|---|---|---|
| EP | 0 448 196 B1 | 12/1997 |
| WO | 2008/132736 A2 | 11/2008 |
| WO | 2010/038217 A1 | 4/2010 |

OTHER PUBLICATIONS

Shouldice, Redmond B., et al., Detection of Obstructive Sleep Apnea in Pediatric Subjects using Surface Lead Electrocardiogram Features, Sleep, vol. 27, No. 4, Jun. 15, 2004;27(4):784-92 (9 pages).

(Continued)

*Primary Examiner* — Navin Natnithithadha
(74) *Attorney, Agent, or Firm* — Merchant & Gould P.C.

(57) ABSTRACT

One method for measuring variability between direct heartbeat data and indirect heartbeat data includes: receiving first heartbeat data from an electrocardiogram over a period of time; receiving second heartbeat data from an indirect measure of heartbeat data over at least a portion of the period of time; calculating, by a computing device, a difference between the first heartbeat data and the second heartbeat data; and comparing the difference to determine a variation.

6 Claims, 5 Drawing Sheets

(56) References Cited

U.S. PATENT DOCUMENTS

| | | | |
|---|---|---|---|
| 5,752,920 A * | 5/1998 | Ogura | A61B 5/02125 600/485 |
| 5,865,756 A * | 2/1999 | Peel, III | A61B 5/02116 600/485 |
| 5,931,790 A * | 8/1999 | Peel, III | A61B 5/022 600/494 |
| 6,120,456 A * | 9/2000 | Oka | A61B 5/02116 600/485 |
| 6,409,675 B1 | 6/2002 | Turcott | |
| 6,491,638 B2 * | 12/2002 | Oka | A61B 5/02125 600/493 |
| 8,500,649 B2 * | 8/2013 | Cho | A61B 5/02007 600/483 |
| 8,506,480 B2 * | 8/2013 | Banet | A61B 5/0408 600/300 |
| 8,571,622 B2 * | 10/2013 | Huiku | A61B 5/14551 600/324 |
| 2001/0003792 A1 * | 6/2001 | Ogura | A61B 5/021 600/500 |
| 2001/0051773 A1 * | 12/2001 | Oka | A61B 5/02125 600/483 |
| 2004/0015091 A1 * | 1/2004 | Greenwald | A61B 5/02125 600/513 |
| 2005/0267362 A1 | 12/2005 | Mietus et al. | |
| 2007/0032733 A1 | 2/2007 | Burton | |
| 2008/0004904 A1 | 1/2008 | Tran | |
| 2011/0137188 A1 | 6/2011 | Kuo et al. | |
| 2011/0301436 A1 | 12/2011 | Teixeira | |
| 2012/0022844 A1 | 1/2012 | Teixeira | |
| 2012/0242501 A1 | 9/2012 | Tran et al. | |
| 2012/0277545 A1 | 11/2012 | Teixeira | |
| 2015/0119654 A1 * | 4/2015 | Martin | A61B 5/0059 600/301 |
| 2015/0119725 A1 * | 4/2015 | Martin | A61B 5/02028 600/479 |

OTHER PUBLICATIONS

Baker, Steven, "Analysis of ECG and SPO2 for Heartbeat," Accessed May 13, 2013 (2 pages).

* cited by examiner

ANALYSIS OF DIRECT AND INDIRECT HEARTBEAT DATA VARIATIONS

BACKGROUND

Heart rate variability is a physiological measure that is used to determine the health of an individual's heart. It is typically measured by examining the periodic nature of the heartbeat, such as the R-R interval of the heart waveform. This measurement can be accomplished directly using an electrocardiogram (ECG) device. The variability between R-R intervals gives the clinician a basic understanding of the function of the central nervous system.

SUMMARY

In one aspect, a method for measuring variability between direct heartbeat data and indirect heartbeat data includes: receiving first heartbeat data from an electrocardiogram over a period of time; receiving second heartbeat data from an indirect measure of heartbeat data over at least a portion of the period of time; calculating, by a computing device, a difference between the first heartbeat data and the second heartbeat data; and comparing the difference to determine a variation.

In another aspect, a method of displaying heart rate variability includes: receiving first heartbeat data from an electrocardiogram over a period of time; receiving second heartbeat data from an indirect measure of heartbeat data over at least a portion of the period of time; selecting a better signal from between the first heartbeat data and the second heartbeat data; calculating, by a computing device, a variability in heartbeats in the better signal; and displaying the variability data.

In yet another aspect, a method of displaying heart rate variability includes: receiving heartbeat data from a pulse oximeter oxygen saturation sensor; compensating for variations in periodicity of the heartbeat data; performing a spectral analysis of the heartbeat data; and displaying the spectral analysis.

DETAILED DESCRIPTION

The present disclosure relates to systems and methods for measuring the variability between different heartbeat data.

In some examples, heart rate variability is calculated using data that is received directly from the heart ("direct heartbeat data"). Direct heartbeat data, often referred to as heart rate, is data obtained using an ECG.

In other examples, heart rate variability (HRV) is calculated using data that derived from the indirect performance of the heart ("indirect heartbeat data," often referred to as pulse rate). An example of indirect heartbeat data is data obtained using a pulse oximeter oxygen saturation sensor or plethysmograph. The indirect heartbeat data is a measure of the blood pulsing due to the pumping of the heart. Other methods for making indirect measurements of heartbeat data include blood pressure measurements, measurements performed by the sensing plate manufactured by Early Sense of Waltham, Mass., where piezo electric sensors in the sensing plate detect heart beats and respiration, using auditory detection at the heart or other convenient location such as the carotid artery, and from pulse pressure detection at an artery such as the brachial, carotid, femoral, radial or princeps pollicis. Detection of heartbeats from blood pressure measurements, from acoustic measurements and from pulse pressure measurements may all be grouped as pressure-based methods.

When direct measures of heartbeat data indicate a beat occurred and indirect measures do not, an abnormal beat, such as a premature ventricular contraction (PVC), may be indicated and may be useful when the direct measure of heart beat does not include waveforms. Such events may be included in the analysis and presentation of the data and used for arrhythmia detection.

Data from direct and indirect measures of heartbeats may come from different sensors that are not synchronized. In this case, cross-correlation may be used to align the two data sets. Once the phase offset for a maximum in the cross-correlation is determined (indicating the data samples are aligned in time), the value of the correlation may be used to as a first measure of the jitter on the indirect heartbeat data compared to the direct heartbeat data.

Figure 1:
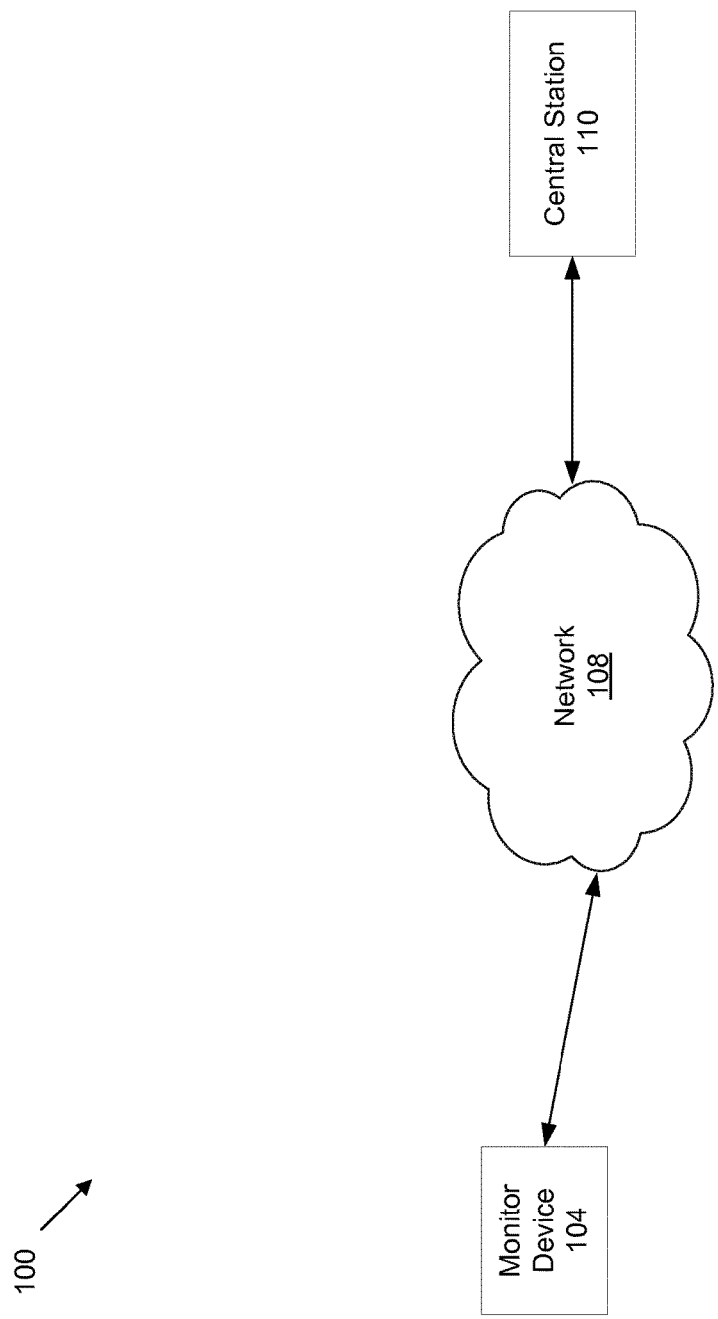
FIG. 1 shows an example system for monitoring a patient.

FIG. 1 is a block diagram illustrating an example system 100 for monitoring a patient.

In this example, the patient is monitored by a monitor device 104. The monitor device 104 is a device that monitors certain physiological attributes associated with the patient. For example, the monitor device 104 monitors various attributes associated with a patient, such as temperature, ECG, oxygen saturation level (SpO2), non-invasive blood pressure (NIBP), end tidal carbon dioxide (ETCO2), and respiration rate. In another example, the monitor device 104 includes a photoplethysmography sensor used to create a photoplethysmogram. Such a sensor can be used to create a high-accuracy and resolution heartbeat measurements. Other sensors can be used.

In this example, the monitor device 104 is a Welch Allyn 1500 Patient Monitor manufactured by Welch Allyn of Skaneateles Falls, N.Y. Other devices can be used.

In this example, the monitor device 104 communicates with a network 108. In one example, the monitor device 104 and the network 108 are part of a CONNEX™ system from Welch Allyn of Skaneateles Falls, N.Y., although other systems can be used. In such an example, the monitor devices communicate through known protocols, such as the Welch Allyn Communications Protocol (WACP). WACP uses a taxonomy as a mechanism to define information and messaging. Taxonomy can be defined as description, identification, and classification of a semantic model. Taxonomy as applied to a classification scheme may be extensible. Semantic class-based modeling utilizing taxonomy can minimize the complexity of data description management by limiting, categorizing, and logically grouping information management and operational functions into families that contain both static and dynamic elements.

The network 108 is an electronic communication network that facilitates communication between the monitor device 104 and a central station 110. An electronic communication network is a set of computing devices and links between the computing devices. The computing devices in the network use the links to enable communication among the computing devices in the network. The network 108 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices.

In various embodiments, the network 108 includes various types of links. For example, the network 108 can include wired and/or wireless links. Furthermore, in various embodiments, the network 108 is implemented at various scales. For example, the network 108 can be implemented as one or more local area networks (LANs), metropolitan area networks, subnets, wide area networks (such as the Internet), or can be implemented at another scale.

The central station 110 is a location at which a caregiver (e.g., a nurse or doctor) can monitor a plurality of patients. For example, the monitor devices 104, 106 send patient data to the central station 110, and the caregiver monitors the patient information at the central station 110. In this example, the central station is a Welch Allyn Acuity® Central Monitoring Station manufactured by Welch Allyn. Other configurations, including mobile applications, are possible.

The monitor device 104 and the central station 110 are computing devices. A computing device is a physical, tangible device that processes data. Example types of computing devices include personal computers, standalone server computers, blade server computers, mainframe computers, handheld computers, smart phones, special purpose computing devices, and other types of devices that process data.

Computing devices can include at least one central processing unit ("CPU"), a system memory, and a system bus that couples the system memory to the CPU. The system memory includes a random access memory ("RAM") and a read-only memory ("ROM"). A basic input/output system containing the basic routines that help to transfer information between elements within the device, such as during startup, is stored in the ROM. The device further includes a mass storage device. The mass storage device is able to store software instructions and data.

The mass storage device and its associated computer-readable data storage media provide non-volatile, non-transitory storage for the device. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the device can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the device.

The computing device can also include an input/output controller for receiving and processing input from a number of other devices, including a keyboard, a mouse, a touch user interface display screen, or another type of input device. Similarly, the input/output controller provides output to a touch user interface display screen, a printer, or other type of output device.

Figure 2:
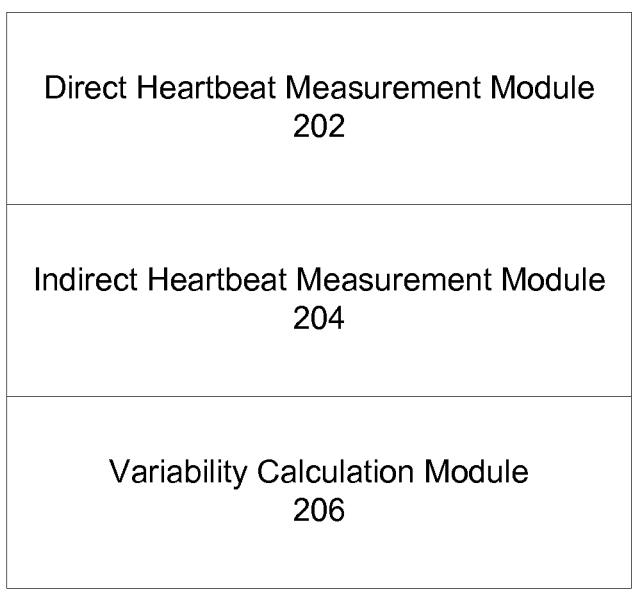
FIG. 2 shows an example device for monitoring a patient from the system of FIG. 1.

Referring now to FIG. 2, additional details about the monitor device 104 are shown. In this example, the monitor device 104 includes a direct heartbeat measurement module 202, an indirect heartbeat measurement module 204, and a variability calculation module 206.

The direct heartbeat measurement module 202 measures direct heartbeat data. An example of direct heartbeat data is data from an ECG. The ECG measures the electrical activity of the heart. The data from the ECG is a direct measure of the activity of the heart.

The indirect heartbeat measurement module 204 measures indirect heartbeat data. Examples of indirect heartbeat data are data from such devices a pulse oximeter oxygen saturation sensor or plethysmograph. Data from the pulse oximeter oxygen saturation sensor (SpO2) is an indirect measure of heart activity because it measures the pulsing of the blood caused by the heart as blood is pumped through the body. Similarly, a plethysmograph provides an indirect measure of heart activity through the measurement of the volume of blood moving through the body. Another example of an indirect measurement of the heart's activity is blood pressure.

The sensors that detect the heartbeat data may transmit it in several formats including waveforms, waveforms annotated with beat detection, times at which beats were detected, an array of elapsed times since the last beat (that is, an array of beat-to-beat intervals). For ECG, the beat-to-beat interval is usually measured from the peak on one R-wave to the peak of the next R-wave and is indicated as the R-R interval. In this specification, R-R interval is used interchangeably with beat-to-beat interval, even when data being analyzed does not include an R-wave, as is the case in a plethysmograph. Plotting the R-R interval versus the heartbeat number (or sample) on the horizontal axis produces what is known as a tachygram, which is a plot of how the R-R interval varies over time.

The variability calculation module 206 calculates the variability (e.g., variability between the direct and indirect heartbeat data and/or heart rate variability) based upon the direct or indirect heartbeat data from the modules 202, 204.

For example, plethsymograph data from the monitor device 104 is analyzed to determine the heart-beat intervals. Given a marker in time for each beat, a spectral analysis may plot the beat-to-beat variation on the y-axis against the beat number on the x-axis. The frequency content of that data is then analyzed in multiple, short-time sequences (typically 500 sets or 256 beats—2 to 5 minute segments) using a fast Fourier transform (FFT), wavelet transform, or similar mathematical operation. The energy of each frequency bin may be mapped to a color and the frequency analysis results are placed along-side one another to produce the frequency-time plot for clinical review that illustrates how the spectral content of the beat-to-beat variations changes over time. This frequency-time plot is often called a spectrogram or a periodogram. Typical HRV results are calculated and displayed after a long period of data collection, typically 24 hours, but calculations and data presentation may be done in near real-time as data are collected and requiring as few as 1 to 10 minutes of data collection for example. This near real-time presentation provides a clinician an early view of the state of the patient's autonomic nervous system.

In some examples, the direct heartbeat data and the indirect heartbeat data are analyzed, and the better signal is used by the variability calculation module 206 to calculate heart rate variability. In such an example, the better of the direct heartbeat data and the indirect heartbeat data is thereupon used for spectrographic analysis. In some cases, a portion or subset of the direct heartbeat data from one period of time might be the better signal and a subset of the indirect heartbeat data from a second period of time might be the better signal. In this case, combining the subsets of the better data might be used.

In other examples, both the direct heartbeat data and the indirect heartbeat data are analyzed. The resulting variability information is used to estimate such aspects as the elasticity/hardening of the arteries. For example, heart activity, such as pulse rate caused by the pumping of the blood, is propagated differently depending on the elasticity of the medium through which the blood is transferred. The elasticity of the arteries carrying the blood can be estimated based upon the difference in variability between direct heartbeat data and indirect heartbeat data. As arteries stiffen, the pulse wave velocity increases and because arterial diameters change less due to pressure as the arteries stiffen, the change in diameter with different pulse pressures decreases. Thus, it is expected that the contribution to the variation in pulse wave velocity due to arterial elasticity decreases and therefore the variability between directly and indirectly measured heartbeat data should decrease as arteries stiffen. By measuring over a sufficient amount of time (e.g., a day or more of data), the elasticity of the artery walls can be estimated. The impact of differences in the time of day and/or impact of activity levels can also be examined.

Obtaining additional physiological measurements, such as blood pressure, and analyzing the combination supports more accurate estimates. In the case of blood pressure, the pulse-transit time changes with pressure, so knowing that blood pressure is higher or lower than on prior measurements gives information about the amount of compensation to make in the R-R measurements due to pressure changes.

In yet another example, the phase delay between the direct heartbeat data and the indirect heartbeat data is examined. The variability is quantified, such as by plotting histograms, spectrograms, or other graphical representations of the beat-to-beat differences. Various conditions are examined to determine maximum and minimum values. In such an example, differences in R-R intervals are taken to build a histogram of the differences to illustrate variation. This can be done over time at various times of day (e.g., sleeping vs. awake), to determine what times of the day exhibit more or less variability between the direct heartbeat data and the indirect heartbeat data.

The amount the phase delay changes may be used to determine how the body is responding to external stimuli. For example, it is known that heart rate variability spectrogram shows less energy, particularly in the HF component, when a patient is experiencing stress, but other factors may cause the low energy. Stress also causes high blood pressure, so by detecting an increase in the phase delay between direct and indirect heartbeat data and also detecting a decrease in the energy of the heart rate variability spectrogram, there are two markers indicating the patient is experiencing stress.

Other markers of health, such as over/under medication, REM sleep cycles, and/or poor overall function of the autonomic nervous system, may be combined with HRV as a means of detection of these conditions. For example, overall low energy in the HRV indicates a poor prognosis for the patient. This coupled with relatively large change in the phase delay may indicate the prognosis is less severe while a relatively small or a progressively decreased change in the phase delay over time may indicate the patient's condition is worse than would be expected from just studying the HRV spectrogram. Further, alerting clinicians the patient is stressed when a blood pressure is measured may explain a reading that is artificially high due stress, for example "white coat syndrome" where patients experience elevated blood pressures in a clinical setting.

Finally, scoring that attempts early detection patient deterioration, such as early warning scores (EWS), modified early warning scores (MEWS) and medical emergency team (MET) activation scores, uses physiological measures such are heart rate, respiration rate, temperature, blood pressure and oxygen saturation. Regardless of the metric, these scoring systems are used as part of a process that has a goal of preventing the patient's condition from deteriorating to the point where a transfer to an intensive care unit is required through use of a rapid response team when at least one activating criterion is met. Acute mental status change and seizures are identified by some hospitals and by the Institute for Clinical Systems Improvement (ICSI) as indications for activating an early response team, however, none of the metrics listed above provide any subjective measure that includes acute mental status. Mental status changes are then subjective and updated only on regular rounds, for example, every four hours. Since R-R variability provides insight into the autonomic nervous system (ANS) including R-R variability as an input to the rapid response team metric provides an objective and automated way to include mental state.

Research has shown that there is an interdependency between intracranial pressure and heart variability. This research suggests that the spectral analysis of R-R variability could be used to detect disorders of autonomic cardiac control in patients with epilepsy. This may be true even for patients that lack abnormal findings during ECG monitoring.

Figure 3:
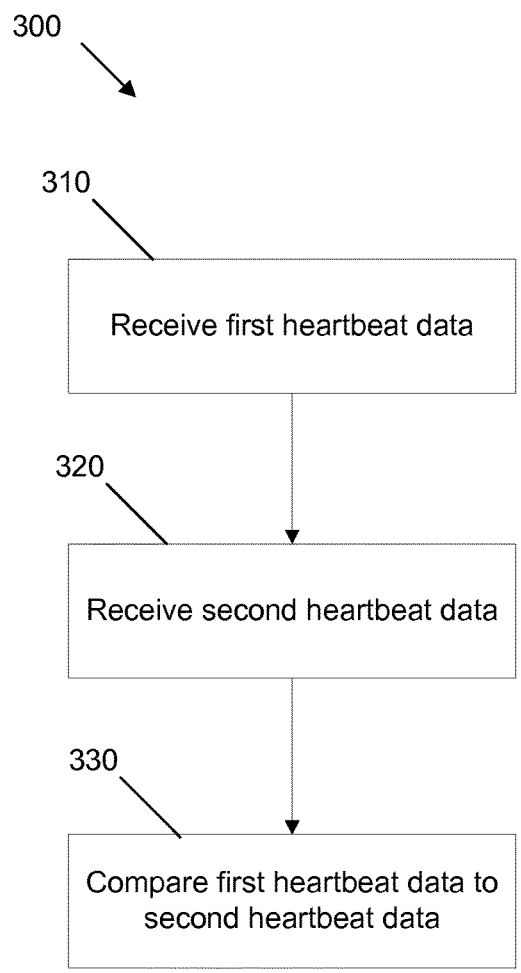
FIG. 3 shows an example method for comparing variability between direct heartbeat data and indirect heartbeat data.

Referring now to FIG. 3, an example method 300 is shown for comparing a variation between direct heartbeat data and indirect heartbeat data.

The method 300 starts at operation 310, when first heartbeat data is received. An example of such heartbeat data is direct heartbeat data. Next, at operation 320, second heartbeat data is received, such as indirect heartbeat data. Operations 310 and 320 can be contemporaneous in nature, in that both the first and second heartbeat data can be received at the same time.

Next, at operation 330, the first heartbeat data is compared to the second heartbeat data to determine the variance therebetween. This can, for example, be conducted at different times of the day and/or for different activity levels. By measuring over a sufficient time period, the changes in variance between the direct and indirect heartbeat data can be ascertained.

Figure 4:
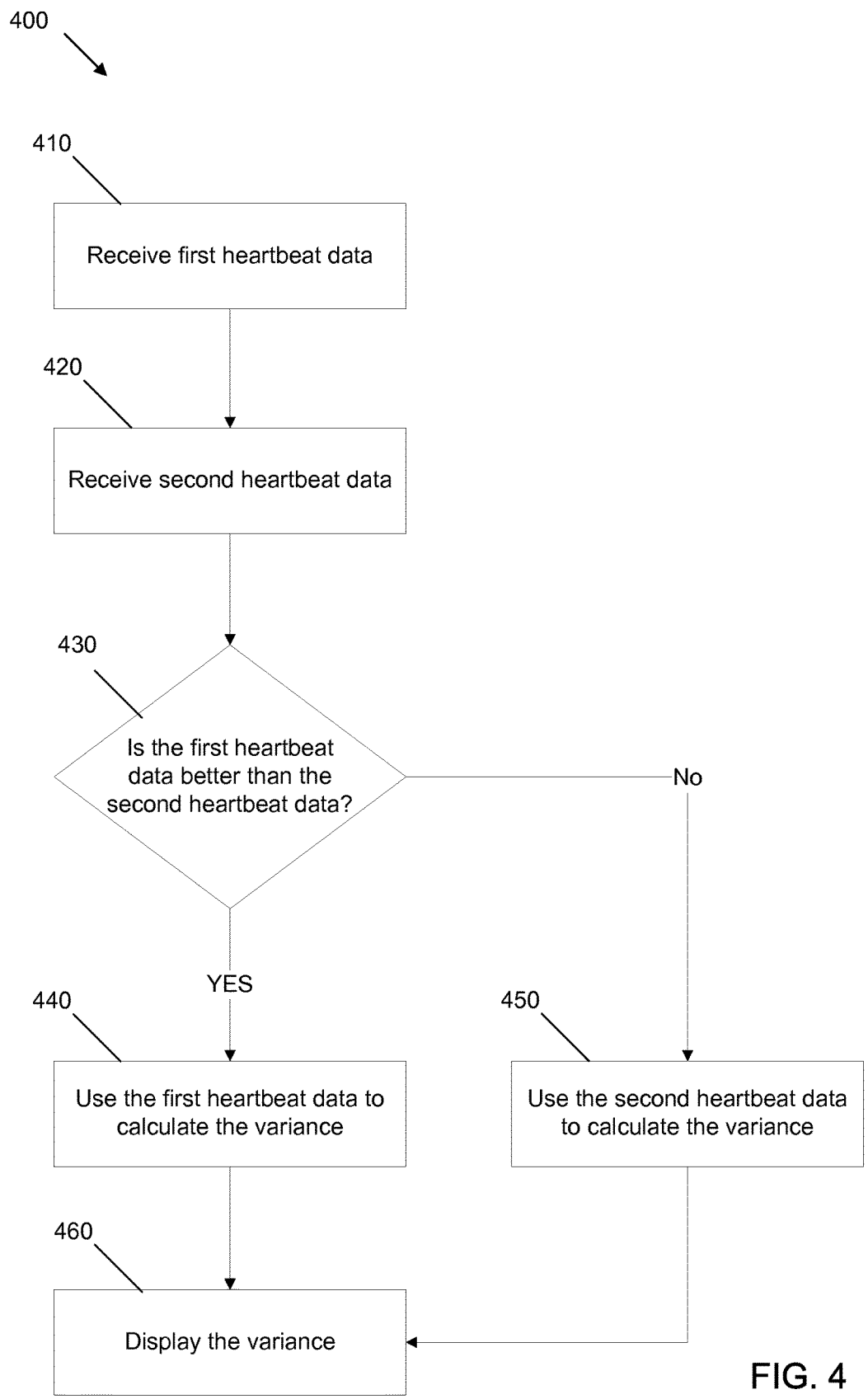
FIG. 4 shows an example method for selecting between direct heartbeat data and indirect heartbeat data to calculate heart rate variability.

Referring now to FIG. 4, an example method 400 is shown for selecting between direct heartbeat data and indirect heartbeat data to calculate heart rate variability.

Initially, at operations 410 and 420, first and second heartbeat data are received. This can be direct heartbeat data and indirect heartbeat data. As noted, the first and second heartbeat data can be received at the same time.

Next, at operation 430, a determination is made regarding which set of data is a better candidate for calculating heart rate variability. In this example, such a determination is made by evaluating the signal to noise ratio. For ECG, the amplitude of the R-wave may be compared to the noise between beats, the energy below 20 Hz may be compared to the energy contained from 20 Hz to the low-pass cut-off of the instrument, and/or the peaks of the power-spectral density (PSD) plot that correspond to the T wave, P wave and the QRS complex may be compared to other peaks in the PSD. Similarly, for pneumoplethysmography and phototplethysmography, the peak may be compared to the amplitude between peaks and/or the spectrum may be analyzed at characteristic frequencies.

If the direct heartbeat data is better, control is passed to operation 440, and the first heartbeat data is used to calculate heartbeat variability. Alternatively if the indirect heartbeat data is better, control is passed to operation 450, and the second heartbeat data is used to calculate heartbeat variability. The determination of the better source of heartbeat data can be made dynamically so that at some times the direct heartbeat data is passed to operation 440 and at other times the indirect heartbeat data is passed to operation 450. Finally, at operation 460, the heart rate variability information is displayed for the caregiver.

In some examples, the determination at operation 430 is performed periodically or in near real time. In such a scenario, should one signal degrade, a switch can be made to the other signal to be used to provide the heart rate variability information and this switch may be noted in the data presentation.

Figure 5:
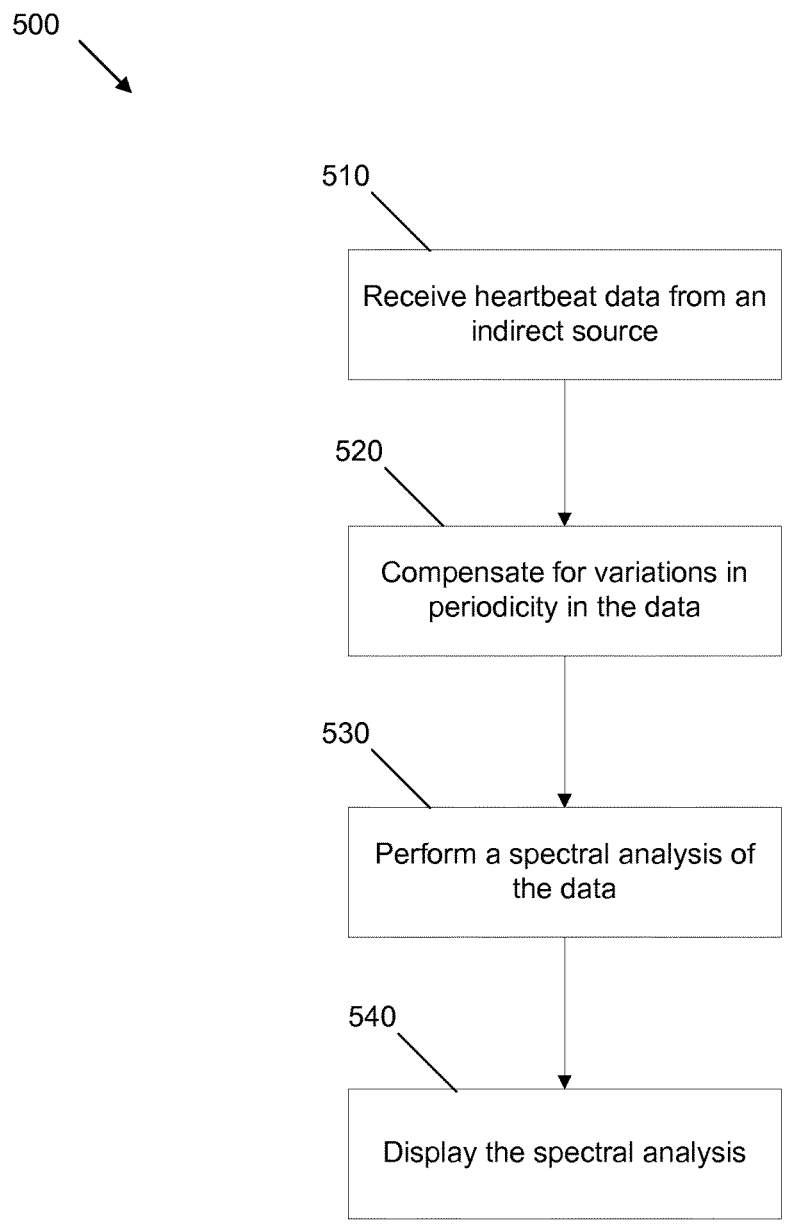
FIG. 5 shows another example method for calculating heart rate variability.

Referring now to FIG. 5, another example method 500 is shown for calculating heart rate variability. In this example, the heartbeat data is manipulated to provide better variability information.

Starting at operation 510, indirect heartbeat data is received, such as from a pulse oximeter oxygen saturation sensor or plethysmograph. Next, at operation 520, a compensation technique is performed to address variations in the periodicity of the data. For example, the indirect heartbeat data may exhibit jitter. Various techniques can be used to compensate for the jitter, such as by filtering and/or using a dejitterizer to minimize the impact of the jitter, using information about the orientation/motions of the patient's body and limbs (as could be measured using inertial sensors including accelerometers and gyroscopes) to compensate for changes due to motion, using blood pressure information to compensate for changes in pulse propagation time due to changes in blood pressure, using skin surface temperature and including medications taken by the patient to provide data for compensation for vasodilation/vasoconstriction, and consideration of sensor location. Generally, the closer the indirect detection is to the heart, the fewer variables there are in the delay of electrical heartbeat to the indirect detection. When compared to R-R intervals, indirect heartbeat detection near the heart may tend to have less jitter in beat-to-beat intervals than indirect heartbeat detection far from the heart. As a specific example of a source of jitter, the pulse transit time to a limb changes by tens of milliseconds depending on whether the limb is above or below the heart. Photoplethysmographic information can also be used to detect changes in the diameter of arteries that in turn may be used to compensate for changes in pulse propagation time. The sensing point may be chosen to minimize effects of vascular, blood pressure, and position change. For example, detecting SPO2 in a large artery such as the femoral artery or carotid. Detecting SPO2 from these large arteries may not be convenient for the patient; however, pulse transit times (PTT) from the thumb have a strong correlation to blood pressure measured with a femoral arterial line.

At operation 530, a spectral analysis of the corrected data is performed. The spectral analysis of either direct or indirect heartbeat measurements may include detection of features including, but not limited to: the very low, low and high frequency bands (approximately 0.03-0.08, 0.9-1.1, and 0.25-0.35 Hz, respectively), REM sleep cycles, stress indicated, autonomic dysfunction, circadian rhythms and ventricular dysfunction. The spectral analysis illustrating the heart rate variability is displayed at operation 540 for the caregiver. The display may include annotations of detected features.

Differential HRV may be used over long periods of time such as months to years to measure and compare changes in the HRV. Differential HRV may average several days' worth of data and compare that to an average taken several years prior. The comparison may be achieved through side-by-side placement of the spectrograms or by subtracting one from the other then analyzing and displaying the result, possibly including annotations of detected health issues. These long-term comparisons may be used to provide early diagnosis. For example in patients with diabetes, this diagnosis may be combined with a decrease in HRV power to provide an early indicator of autonomic neuropathy before other clinical expressions are detected. Long-term comparisons may also be used to detect changes such as differences in the day-to-night variations in the R-R interval that indicate a myocardial infarction.

Ideally, a feature of the indirect heartbeat waveform is identified that minimizes the jitter in time between when a heartbeat is detected using ECG (ECG heartbeat picking typically defines the peak of the R-wave as the point in time where a heartbeat occurred) and when a heartbeat is picked from an indirect source such as pulse pressure, audio or SPO2. Considering SPO2 waveforms as an example, features include the peak of the plethysmograph, the notch in the descending limb of the plethysmograph, a percentage of the amplitude to the peak (rising or falling), or similar feature. Any of these, or a combination thereof, may be used as a feature for detecting the heartbeat. Considering audio detection of the heartbeat, the characteristic "lub-dub" sounds cause by the closing of the AV valves and the semilunar valves, respectively has two distinct peaks and a distinct valley among other features. Any of these, or a combination thereof, may be used as a feature for detecting the heartbeat.

Whether the heartbeat data is detected directly or indirectly, determining where the features such as peaks, valleys, and/or the overall waveform occurs in time as part of the beat picking can be accomplished by slope detection, matched filters, frequency-domain analysis, using a comb function with spacing based on the prior detected beats, and the like. Heuristics may be used to determine which signal is more reliable. For example, a sudden change in noise or detected beat interval may occur on ECG signals detected from a patient straining forward to reach a meal tray indicating that SPO2 should be used.

Indirect heartbeat measurements may be used to qualify ECG heartbeats detected in the presence of such noise. For example if the system learns that the time from R-wave peak to SPO2 plethysmograph peak occurs at a range from $t=t0$ to $t=t1$, then during periods of noise on the ECG signal, this time frame may be used as a detection window to improve both the specificity of the ECG heartbeat detection. That is, exclude any R-wave detections outside the time window $t=t0$ to $t=t1$ prior to the SPO2 beat detection. There may be cases where one source is more reliable than the other. In this case, the beat detection data from the two sources may be combined by selecting the most reliable subsets of each data set.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A method for measuring variability between direct heartbeat data and indirect heartbeat data, the method comprising:
   receiving first heartbeat data from an electrocardiogram over a period of time;
   receiving second heartbeat data from an indirect measure of heartbeat data over at least a portion of the period of time;
   calculating, by a computing device, a difference between the first heartbeat data and the second heartbeat data;
   comparing, by the computing device, the difference to determine a variation;
   estimating, by the computing device, an elasticity of arteries of an individual by analyzing the difference between the first heartbeat data and the second heartbeat data over time;
   selecting, by the computing device, subsets of the first heartbeat data and subsets of the second heartbeat data;
   performing, by the computing device, a spectral analysis of the selected subsets of the first heartbeat data and subsets of the second heartbeat data; and
   presenting, by a display device, the spectral analysis, wherein the spectral analysis includes detection of features of the selected subsets of the first heartbeat data and subsets of the second heartbeat data.

2. The method of claim 1, further comprising:
   plotting graphical representations of beat-to-beat differences;
   performing measurements at different conditions; and
   determining more or less variance based upon the different conditions.

3. The method of claim 1, further comprising using a pulse oximeter oxygen saturation sensor to provide the indirect measure.

4. The method of claim 1, further comprising using a pressure sensor to provide the indirect measure.

5. The method of claim 1, wherein the spectral analysis is presented in near real-time.

6. The method of claim 1, wherein the selecting subsets includes selecting a desired signal from between the first heartbeat data and the second heartbeat data.

* * * * *